United States Patent [19]

Amann

[11] 4,180,393
[45] Dec. 25, 1979

[54] COMPOSITION FOR CONTROLLING PLANT GROWTH IN VITICULTURE

[75] Inventor: Fritz Amann, Ober-Ramstadt, Fed. Rep. of Germany

[73] Assignee: SKW Trostberg Aktiengesellschaft, Trostberg, Fed. Rep. of Germany

[21] Appl. No.: 923,458

[22] Filed: Jul. 10, 1978

[30] Foreign Application Priority Data

Aug. 19, 1977 [DE] Fed. Rep. of Germany ....... 2737454

[51] Int. Cl.$^2$ ............................................. A01N 11/00
[52] U.S. Cl. ........................................... 71/78; 71/65; 71/76
[58] Field of Search ................................. 71/65, 78, 76

[56] References Cited

FOREIGN PATENT DOCUMENTS

| | | | |
|---|---|---|---|
| 1642343 | 5/1971 | Fed. Rep. of Germany | 71/65 |
| 2040119 | 2/1972 | Fed. Rep. of Germany | 71/65 |
| 1265244 | 3/1972 | United Kingdom | 71/65 |

OTHER PUBLICATIONS

Giovannetti et al., "L'Azione Anticrittogamica della, etc.," (1976), L'Agric. Ital., 104, pp. 1–15, (1976).
Rottini et al., "Azione Antimitotica della, etc.," (1961), La Chimica e l'Industria, pp. 1–6, (1961).
Vilsmeier et al., "Cyanamide Treatment for Control, etc.;" (1975), CA 83 No. 127526v.
Bauer et al., "Destroying Stray Shoots, etc.;" (1972), CA 77 No. 71446a, (1972).
Patzholz et al., "Killing of Side Shoots, etc.;" (1972), CA 77 No. 1858n, (1972).
Giovannetti et al., "The Antifungal Action, etc.;" (1976), CA 85 No. 172587t, (1976).
Rotini et al., "Mitricidal Action, etc.;" (1961), CA 55, p. 15817, (1961).

*Primary Examiner*—Glennon H. Hollrah
*Attorney, Agent, or Firm*—Curtis, Morris & Safford

[57] ABSTRACT

The "wild" shoots on grape vines are eliminated by applying to the vines an aqueous solution containing from 1% to 5% by weight of cyanamide.

3 Claims, No Drawings

COMPOSITION FOR CONTROLLING PLANT GROWTH IN VITICULTURE

The present invention relates to a composition for controlling plant growth in viticulture, as well as to a method of using such a composition.

A considerable part of the total work involved in viticulture consists of leaf work. This work includes the pinching off of undesired vine shoots and the fastening and pruning or thinning out of the vines. These tasks constitute a considerable amount of work since they must be carried out within a relatively short specific period of time.

Previous attempts to mechanize this work have not yet been successful. (See D. Maul: "Moglichkeiten zur Mechanisierung der Laubarbeiten" in "Der Deutsche Weinbau", No. 18, 1977). Also chemical methods for carrying out this work have not previously been known. In accordance with the present state of the art, therefore, this leaf work is carried out by hand. The shortage of workers and the cost of labor impose a considerable burden on the vine grower.

The basis of the vine is the "stem", which consists of perennial wood, so-called "old wood". The fruit-bearing shoots develop at the upper end of the stem from the buds of annual shoots. Shoots, however, can be formed not only from annual wood but also directly from the perennial old wood of the stem. Such shoots, also known as "wild shoots", bear no fruit and must be removed by hand. This work is referred to as "pinching off the stem shoots."

It is known from West German Provisional Pat. No. 1,642,343 that cyanamide can be used to kill ground sideshoots of hop plants. In this case, however, there are concerned vegetative shoots which develop from the underground portion of the stem of the hop plant. After breaking through the surface of the earth, the side shoots are treated with cyanamide but the underground stem itself does not come directly into contact with cyanamide.

The object of the present invention is to reduce the amount of manual leaf work in viticulture by using an agent for controlling undesired plant growth. This purpose is achieved by using an agent for the chemical "pinching-off" of undesired stem shoots in viticulture, i.e., a chemical composition containing an agent for suppressing the growth of undesired stem shoots, which agent is cyanamide. We were surprised to find that the active substance, cyanamide, can be used for killing stem shoots of grape vines without adversely affecting the other vegetative and generative developments of the vine. There are fundamental phytomorphological differences between the stem shoots of vines and the ground shoots of hop plants. The shoots of grape vines develop on the part of the plant which is above the ground while the ground shoots of the hop plant, on the other hand, develop from the underground part of the stem. Furthermore, when cyanamide is used for killing the shoots of vines it is not possible to prevent the stem also being contacted by the cyanamide. The active substance, cyanamide, completely destroys those shoots which are directly contacted. It has been found that the stem which is also contacted by the cyanamide at the same time is not damaged. The further development of the stem, the vegetative growth, the grape blossoms, and the development of the grapes are not adversely affected. It is known, and of particular advantage for the use of cyanamide for controlling undesired plant growth, that the active substance decomposes rapidly and completely on the plant and in the earth so that no undesired residues remain either in the ground or in the grapes.

The active substance, cyanamide, is desirably applied in a growth-suppressing amount and in the form of a dilute aqueous 50% solution by spraying. The concentration of cyanamide in the dilute spray solution may be 1-5% by weight, preferably 1.5 to 3% by weight. This means that with about 1000 liters of spray mixture per hectare, 10 to 50 and preferably 15 to 30 kg of cyanamide are applied per hectare. The shoots to be removed must be thoroughly wetted with this spray solution, each stem requiring about 100 to 150 ml of spray mixture. By this method the undesired shoots of all common kinds of graphs can be killed. In the following Examples 1-5, this action is shown on the two most important types of grapes, Riesling and Silvaner.

EXAMPLE 1

Place of experiment: Haardter Mandelring
Type of grape: Riesling/5 BB
Size of lot: 12 vines
Length of the shoots treated: about 4–8 cm
Number of shoots per vine: average 10–12
Height of vines sprayed: about 60 cm The cyanamide was applied in aqueous solution containing 1.5, 2.0 and 2.5 weight % of cyanamide.

| Treatment on May 29th | Burning of the treated shoots in % | | New sprouting from shoot residues June 24 |
|---|---|---|---|
| | June 1 | June 8 | |
| Untreated | 0 | 0 | — |
| 1.5 wt. % | 85 | 90 | none (shoot residues completely removed) |
| 2.0 wt. % | 90 | 95 | |
| 2.5 wt. % | 95 | 100 | |

No damage to the shoots above the spray zone was noted. Further development of the vine, blossoms, and development of grapes were not adversely affected.

EXAMPLE 2

Place of experiment: Neustadt/LFA
Type of grape: Silvaner/5 BB, wide-spacing
Size of lot: 2 lots of 12 vines each
Length of shoots treated: 20–60 cm
Height of vines: 1.10–1.20 m Aqueous solutions containing 1.5 wt. % and 2.0 wt. % of cyanamide were used.

| Treatment on May 25 | Burning of the treated shoots | | Number of new shoots per stem July 28 |
|---|---|---|---|
| | May 27 | June 1 | |
| Untreated | — | — | 2.5 |
| 1.5 wt. % | shoot tips completely killed | Shoot tips and leaves of the shoots completely killed. Shoot base incipient burning. | 2.0 |
| 2.0 wt. % | | | 1.0 |

No damage to the vine or above the spray zone was noted. No adverse effect on the further growth was observed.

EXAMPLE 3

Place of experiment: Geinsheim/Adam
Type of grape: Silvaner, normal planting
Lot size: 2 lots of 10 vines each
Length of shoots treated: 15–20 cm (max. 50 cm)
Height of stem of vine: 80 cm A 2% by weight aqueous solution of cyanamide was used.

| Treatment on | Burning of the shoots | | Number of new shoots |  |
|---|---|---|---|---|
| May 27 | June 3 | June 7 | July 2 | |
| | | | per lot | per vine |
| Untreated | — | — | 34 | 1.7 |
| Cyanamide solution | shoot tips killed, leaves discolored brown | all shoots completely killed | 16 | 0.8 |

EXAMPLE 4

Place of experiment: Neustadt/Geinsheim
Type of grape: Silvaner
Size of lot: 2 lots of 10 vines each
Height of stem of vines: about 80–100 cm A 2% by weight aqueous cyanamide was used.

| Treatment | Time of Treatment | Number of shoots remaining (relative) | | |
|---|---|---|---|---|
| | | May 30 | June 7 | June 21 |
| Untreated | — | 100 | 100 | 100 |
| Cyanamide solution | May 23 with 5 cm length of shoot | 0 | 0 | 0 |
| | May 30 with 10 cm length of shoot | — | 50 | 5 |
| | June 7 with 15 cm length of shoot | — | — | 50 |

EXAMPLE 5

Place of experiment: Geinsheim/Adam
Type of grape: Silvaner
Size of lot: 2 lots of 10 vines each
Height of stem of vines: about 80 cm A 2% by weight aqueous cyanamide was used.

| Treatment | Time of Treatment | Number of vine shoots remaining (relative) June 23 | Number of new shoots (relative) August 8 |
|---|---|---|---|
| Untreated | — | 100 | 100 |
| Cyanamide solution | May 27 with shoot length of 5–8 cm | 25 | 33 |
| | June 4 with shoot length of 10–15 cm | 25 | 25 |

From the foregoing Examples it is apparent that aqueous cyanamide solutions are selectively effective in suppressing the growth of "stem shoots" in viticulture.

I claim:

1. The method of eliminating the wild shoots on grape vines without damaging the stems of the vines which comprises applying to the vines an aqueous solution containing a growth suppressing amount of cyanamide.

2. A method according to claim 1 wherein said solution contains from 1% to 5% by weight of cyanamide.

3. The method of eliminating wild shoots on grape vines without damaging the stems of the vines which comprises applying to the vines an aqueous solution of cyanamide containing 1.5% to 3% by weight of cyanamide.

* * * * *